United States Patent [19]

Karjalainen et al.

[11] 4,275,072

[45] Jun. 23, 1981

[54] 2,6-DICHLOROPHENYL-SUBSTITUTED AMINO-IMIDAZOLE DERIVATIVES AND USE AS HYPERTENSIVE AGENTS

[75] Inventors: Arto Karjalainen; Kauko Kurkela, both of Oulu, Finland

[73] Assignee: Farmos Group, Ltd., Turku, Finland

[21] Appl. No.: 93,247

[22] Filed: Nov. 13, 1979

Related U.S. Application Data

[63] Continuation-in-part of Ser. No. 934,371, Aug. 16, 1978, abandoned.

[51] Int. Cl.$^3$ .................. A61K 31/415; C07D 233/54
[52] U.S. Cl. .............................. 424/273 R; 548/315; 548/337
[58] Field of Search ............................. 548/315, 337; 424/273 R

[56] References Cited

PUBLICATIONS

Jen. et al., Journal of Medicinal Chemistry, vol. 18, No. 1, (1975) pp. 90–99.

*Primary Examiner*—Henry R. Jiles
*Assistant Examiner*—Robert C. Whittenbaugh
*Attorney, Agent, or Firm*—Burns, Doane, Swecker & Mathis

[57] ABSTRACT

The 2,6-dichlorophenyl-substituted amino-imidazole derivatives 1-(2',6'-dichlorophenyl)-2-amino-4-methyl-imidazole, 2-(2',6'-dichloroanilino)-4-methyl-imidazole, their non-toxic, pharmaceutically acceptable, acid addition salts and mixtures thereof, exhibit excellent antihypertensive activity which makes the derivatives particularly suitable for treatment of high blood pressure in mammals.

The derivatives may be prepared in either of two processes. The first process involves the sequential reaction of a known starting material with ammonia and a halogenated acetone which may be followed by separation of the formed isomers. The second process involves the decarboxylation of the novel intermediates 4-[1-(2',6'-dichlorophenyl)-2-amino)]-imidazoleacetic acid or 4-[2-(2',6'-dichloroanilino)]-imidazoleacetic acid or mixtures thereof. Such intermediates, their lower alkyl esters, their non-toxic, pharmaceutically acceptable acid addition salts or mixtures thereof may also be employed as a diuretic agent.

The derivatives are employed in an effective amount and are typically combined with a pharmaceutical carrier. Administration of the derivatives may be accomplished either orally or parenterally.

12 Claims, No Drawings

2,6-DICHLOROPHENYL-SUBSTITUTED AMINO-IMIDAZOLE DERIVATIVES AND USE AS HYPERTENSIVE AGENTS

RELATED APPLICATIONS

The present application is a continuation-in-part of copending United States application Ser. No. 934,371 filed on Aug. 16, 1978, now abandoned.

BACKGROUND OF THE INVENTION

1. Field of the Invention

This invention relates to certain novel 2,6-dichlorophenyl substituted amino-imidazole derivatives and their non-toxic, pharmaceutically acceptable acid addition salts. This invention also relates to a process for preparing the derivatives and to a process for employing the derivatives and their salts as anti-hypertensive agents in mammals. This invention further relates to novel intermediates and their non-toxic, pharmaceutically acceptable acid salts and to a process of using such compounds as diuretic agents in mammals.

2. Summary of the Prior Art

It is known in the art that a number of imidazole compounds and their derivatives exhibit pharmacological properties. Thus, for example, U.S. Pat. No. 2,944,061 describes derivatives, such as 1-(2-hydroxyethyl)-2-methyl-5-nitroimidazole (i.e., metronidazole) or their acid addition salts, as exhibiting antiprotozoal activity.

A further type of imidazole derivative which may be used as an antagonist to H-2 type histamine receptors is disclosed in British Pat. No. 1,397,436. Compounds which exemplify this type of imidazole derivative include N-cyano-N'-methyl-N''-[2-[[(5-methyl-1H-imidazol-4-yl) methyl]thio]ethyl]guanidine (i.e., cimetidine).

Imidazoline derivatives having pharmacological properties are also known in the art. These derivatives are structurally different from the imidazole derivatives primarily by possessing only a single carbon to carbon covalent bond within the ring structure. Exemplary of the imidazoline derivatives are the vasoconstrictor and adrenergic agents 2-benzyl-2-imidazoline (i.e., tolazoline) and 2-(1-naphthylmethyl)imidazoline (i.e., naphazoline) as described in U.S. Pat. No. 2,161,938.

Another example of a pharmacologically active imidazoline derivative is set forth in U.S. Pat. No. 3,202,660. This patent describes 2-(2,6-dichloroanilino)-2-imidazoline (i.e., clonidine) as being an anti-hypertensive agent.

The preparation and anti-hypertensive activity of clonidine and various phenyl substituted derivatives of clonidine is discussed in P.B.M.W.M. Timmermans et al, J. of the Royal Netherlands Chem. Soc., 96/2, Feb. 1978. Other clonidine related compounds which exhibit anti-hypertensive and anti-secretory activity are described in Jen et al, J. of Medicinal Chem., Volume 18, No. 1 (1975) and German Offenlegungsschuft No. 2,618,756.

It has been found that a number of the pharmacologically active imidazole and imidazoline derivatives possess serious drawbacks. Thus, for example, it is recognized that some of the known derivatives do not display anti-hypertensive activity or are relatively toxic which makes dosage regulation critical. Other derivatives exhibit undesirable side effects. Illustrative of the latter type of such derivatives is clonidine itself which causes a temporary rise in blood pressure at the beginning of administration.

OBJECTS AND SUMMARY OF THE INVENTION

It is therefore an object of the present invention to provide certain novel imidazole derivatives and their acid addition salts which eliminate or substantially reduce the problems of the prior art.

It is a more specific object of the present invention to provide certain non-toxic imidazole derivatives and their non-toxic, pharmaceutically acceptable acid addition salts which are useful as anti-hypertensive agents.

It is another object of the present invention to provide novel intermediates which are useful in the preparation of the non-toxic imidazole derivatives and their non-toxic, pharmaceutically acceptable acid addition salts and which are themselves useful as diuretic agents.

It is yet another object of the present invention to provide a process for preparing the non-toxic imidazole derivatives.

It is a further object of the present invention to provide a process for treating mammals with the non-toxic imidazole derivatives and their non-toxic, pharmaceutically acceptable acid addition salts.

In accordance with one aspect, the present invention provides novel 2,6-dichlorophenyl-substituted amino-imidazole derivatives having anti-hypertensive properties selected from the group consisting of 1-(2',6'-dichlorophenyl)-2-amino-4-methyl-imidazole and 2-(2',6'-dichloroanilino)-4-methyl-imidazole, their non-toxic, pharmaceutically acceptable acid addition salts, and mixtures thereof.

In another aspect, the present invention provides a process for the preparation of 2,6-dichlorophenyl-substituted amino-imidazole derivatives. The process comprises:

(a) dissolving a starting material selected from the group consisting of: (1) 2,6-dichlorophenyl isocyanide dichloride, (2) S-methyl-2,6-dichlorophenyl isothiuronium iodide, (3) 2,6,-dichlorophenyl cyanamide, (4) 2,6-dichlorophenyl guanidine, and (5) mixtures thereof in a nonaqueous solvent;

(b) contacting the mixture with gaseous ammonia, (c) adding a halogenated acetone in the continued presence of gaseous ammonia;

(d) heating the resulting mixture; and (e) recovering 1-(2',6'-dichlorophenyl)-2-amino-4-methyl-imidazole and 2-(2',6'-dichloroanilino)-4-methyl-imidazole.

In a further aspect, the present invention provides a process for the preparation of 2,6-dichlorophenyl -substituted amino-imidazole derivatives. The process comprises subjecting a member selected from the group consisting of

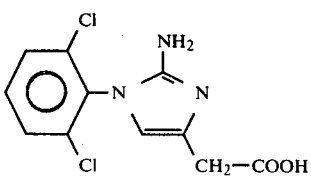

(a)

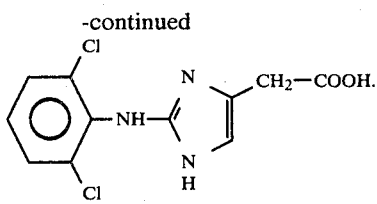

and (c) mixtures thereof, to decarboxylation.

In a still further aspect, the present invention provides a process for treating a mammal having a hypertensive condition. The process comprises administering to said mammal an effective amount of a composition selected from the group consisting of 1-(2′,6′-dichlorophenyl)-2-amino-4-methyl-imidazole, 2-(2′,6′-dichloroanilino)-4-methyl-imidazole, their non-toxic, pharmaceutically acceptable acid addition salts and mixtures thereof.

In yet a further aspect, the present invention provides a process for treating a mammal with an effective amount of a diuretic agent selected from the group consisting of 4-[1-(2′,6′-dichlorophenyl)-2-amino]-imidazoleacetic acid, 4-[2-(2′,6′-dichloroanilino)]-imidazoleacetic acid, 4-[1-(2′,6′-dichlorophenyl)-2-amino]-imidazoleacetic acid lower alkyl ester, 4-[2-(2′,6′-dichloroanilino)]-imidazoleacetic acid lower alkyl ester and mixtures thereof.

Other objects, aspects and advantages of the present invention will become apparent to those of ordinary skill in the art in view of the following description of the preferred embodiments.

DESCRIPTION OF THE PREFERRED EMBODIMENTS

As sated above, the present invention relates to certain non-toxic imidazole derivatives and their non-toxic, pharmaceutically active acid addition salts. The imidazole derivatives are specifically 1-(2′,6′-dichlorophenyl)-2-amino-4-methyl-imidazole (I) and 2-(2′,6′-dichloroanilino)-4-methyl-imidazole (II) which are respectively illustrated by the following formulas:

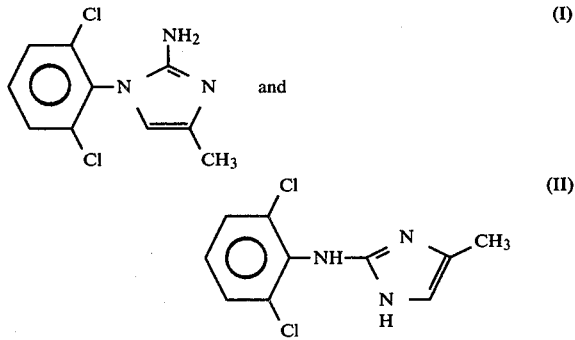

As will be apparent to those of ordinary skill in the art, compounds I and II are isomers which, by definition, have the same molecular weight and number and type of atoms. Preparation of isomeric compounds I and II may be accomplished by either of two processes. In either process, the starting material is a known compound such as 2,6 dichlorophenyl isocyanide dichloride (III):

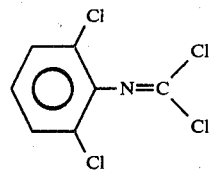

Other known compounds which may also be used in the preparation of isomeric compounds I and II include S-methyl-2,6-dichlorophenyl isothiouronium iodide (IV), 2,6-dichlorophenylcyanamide (V) and 2,6-dichlorophenyl guanidine (VI) having the respective formulas:

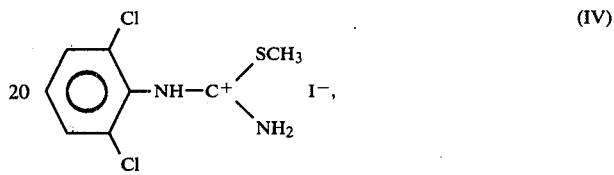

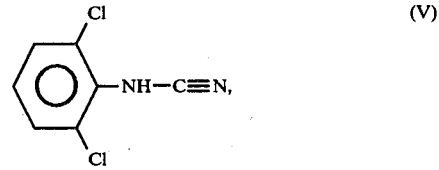

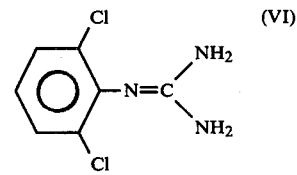

Mixtures of the compounds may also be employed.

In the first process of preparing isomeric compounds I and II, the starting material (e.g., 2,6-dichlorophenyl isocyanide dichloride) is dissolved in a suitable, nonaqueous solvent, such as hexane, toluene, xylene, tetrachloromethane, dioxane, tetrahydrofuran and, preferably, absolute ethanol. The mixture is contacted with gaseous ammonia for a period of time ranging from about 0.5 to about 3 hours and is typically added for about one hour. Ammonia addition is generally accomplished by bubbling the ammonia through the mixture at ambient conditions.

While maintaining ammonia addition, from about 10 to about 20%, based on the weight of the starting material, of a halogenated acetone, such as bromoacetone or chloroacetone, is added to the mixture. Although the halogenated acetone may be added in pure form, it is generally diluted with a non-aqueous solvent (e.g., additional absolute ethanol) to form a solution comprised of from about 10 to about 30% by weight of the halogenated acetone.

The temperature of the resulting mixture is then raised to about its boiling point. Ammonia addition is maintained during the heating step for a period of time ranging from about 1 to about 3 hours, typically for about 2 hours and then terminated. Heating is continued until the mixture is evaporated to dryness.

To recover isomeric compounds I and II, the resulting residue is dissolved in a mixture comprising from about 50 to about 70% by weight of a dilute mineral acid, such as sulfuric acid, nitric acid, or preferably, hydrochloric acid and correspondingly from about 30 to about 50%, by weight of an organic solvent, such as butyl acetate, propyl acetate and, preferably, ethyl acetate. The term "dilute" is used to mean acids of from about 0.5 to about 2 N.

The organic (e.g., ethyl acetate) phase is separated, typically by decantation, from the aqueous phase. The pH of the aqueous phase is increased to above about 7.0 by adding an alkaline agent such as ammonia, sodium hydroxide or sodium carbonate. The aqueous phase is then extracted with chloroform or another organic solvent, such as ethyl acetate. The extract is evaporated to dryness thereby yielding a mixture of crude 1-(2',6'-dichlorophenyl)-2-amino-4-methylimidazole (I) and 2-(2',6'-dichloroanilino)-4-methyl-imidazole (II).

The mixture of isomeric compounds I and II may be separated by conventional techniques such as by column chromatography using a column of silica gel and ethyl acetate and methanol, respectively, as elutants.

The alternate process for preparing isomeric compounds I and II initially involves dissolving a suitable starting material, such as compounds III, IV, V or VI, or mixtures thereof, in a non-aqueous solvent, such as hexane, toluene, xylene, tetrachloromethane, dioxane, tetrahydrofuran and, preferably, absolute ethanol, at a temperature of from about 10° to about 25° C., usually at room temperature. The resulting mixture, is contacted with gaseous ammonia for a period of time extending from about 0.5 to about 2 hours, typically for about one hour. Ammonia addition is again typically accomplished by bubbling the ammonia through the mixture at ambient conditions.

While maintaining ammonia addition, a halogenated acetoacetic acid lower alkyl ester, in either pure form or diluted in a non-aqueous solvent (e.g., additional absolute ethanol), is added. As used herein the term "halogenated acetoacetic acid lower alkyl ester" includes those compounds wherein the halogen radical is chloro, bromo or iodo and the lower alkyl radical is ethyl, propyl or butyl. The preferred ester is chloroacetoacetic acid ethyl ester. The resulting intermediate is cyclized by raising the temperature of the mixture to about its boiling point under continued ammonia addition for about another six hours. The mixture is then cooled and filtered, with the mother liquor next being evaporated to dryness, typically under reduced pressure.

The residue from the mother liquor is dissolved in a mixture of a dilute mineral acid and organic solvent such as those discussed above with respect to the first process. The organic phase is separated, typically by decantation, from the aqueous phase. The aqueous phase is washed with additional organic solvent, rendered alkaline (i.e., to a pH of about 8-10) with known alkaline agents, such as sodium hydroxide, sodium carbonate or ammonia, and extracted with chloroform. The chloroform extract is then washed with water, dried over a desiccant, such as sodium carbonate or sodium sulfate, and heated to complete dryness, typically under reduced pressure.

The resulting solid residue is triturated with a warm organic solvent, generally ethyl acetate, cooled and filtered. The filter residue is primarily a mixture of 4-[1-(2',6'-dichlorophenyl)-2-amino]-imidazoleacetic acid lower alkyl ester and 4-[2-(2',6'-dichloroanilino)]-imidazoleacetic acid lower alkyl ester wherein the lower alkyl is ethyl, propyl or butyl. These novel intermediates as well as their acid counterparts have been found to exhibit diuretic activity, as more fully discussed below. Hence, the term "intermediates" is collectively used herein primarily to distinguish the various compounds.

The filter residue is dissolved in a mixture comprised of from about 30 to about 60% by weight of a ketone, preferably acetone, and correspondingly from about 70 to about 40% by weight of butyl acetate, propyl acetate, or, preferably ethyl acetate and the resulting solution is acidified. Acidification is generally accomplished by passing a gaseous non-aqueous mineral acid such as gaseous hydrogen chloride through the solution until the pH of the solution reaches about 4-5. The acidified solution is cooled and filtered to yield a filter residue and liquor.

The filter residue is substantially pure 4-[2-(2',6'-dichloroanilino)]-imidazoleacetic acid lower alkyl ester hydrochloride. To obtain the related ester (i.e., 4-[2-(2',6'-dichloroanilino)]-imidazoleacetic acid lower alkyl ester), the filter residue is dissolved in water and contacted with gaseous ammonia.

The remaining liquor is evaporated to dryness typically under reduced pressure. The resulting solid matter is dissolved in water, rendered alkaline by contacting the mixture with gaseous ammonia and filtered. The filtered precipitate is substantially pure 4-[1-(2',6'-dichlorophenyl)-2-amino]-imidazoleacetic acid lower alkyl ester which may be further purified by recrystallization, typically by using ethyl acetate, propyl acetate or, preferably, n-butyl acetate.

To obtain isomeric compounds I or II from the related prepared ester compounds, the ester compound is first hydrolyzed to form the novel acid intermediate, namely 4-[1-(2',6'-dichlorophenyl)-2-amino]-imidazoleacetic acid (Ia) or 4-[2-(2',6'-dichloroanilino)]-imidazoleacetic acid (IIa). This may be accomplished by suspending the ester compound in a concentrated mineral acid (e.g., hydrochloric acid), boiling the suspension for about 0.5 to about 2.0 hours, typically for about one hour and cooling the suspension to about room temperature. The term "concentrated" defines acids of from about 6 to about 12 N. The cooled suspension is neutralized with an alkaline agent, such as gaseous ammonia, and is filtered. The precipitate comprises the related acid compound Ia or IIa.

The related acid compound is then decarboxylated to isomeric compound I or II. Decarboxylation of acid compounds Ia or IIa is achieved by suspending the acid compound in a high boiling organic solvent such as glycol, glycerol, or other known inert, high boiling solvents or a concentrated mineral acid, such as hydrochloric acid, and heating the suspension to a temperature of from about 100° to about 200° C. (e.g., about 180° C.) under agitation and refluxing conditions for about 4 to about 8 hours. After cooling the suspension to about room temperature, an alkaline agent, such as a solution of sodium hydroxide or sodium carbonate, is added to render the suspension alkaline. The suspension is then extracted with a suitable solvent, such as chloroform trichloromethane or ethyl acetate, and the extract is evaporated to dryness thereby yielding isomeric compound I or II. To obtain a purer product, the compound may be recrystallized from a suitable solvent such as isopropanol.

The reaction scheme, employing 2,6-dichlorophenyl isocyanide dichloride and chloroacetoacetic acid ethyl ester, may be illustrated as follows:

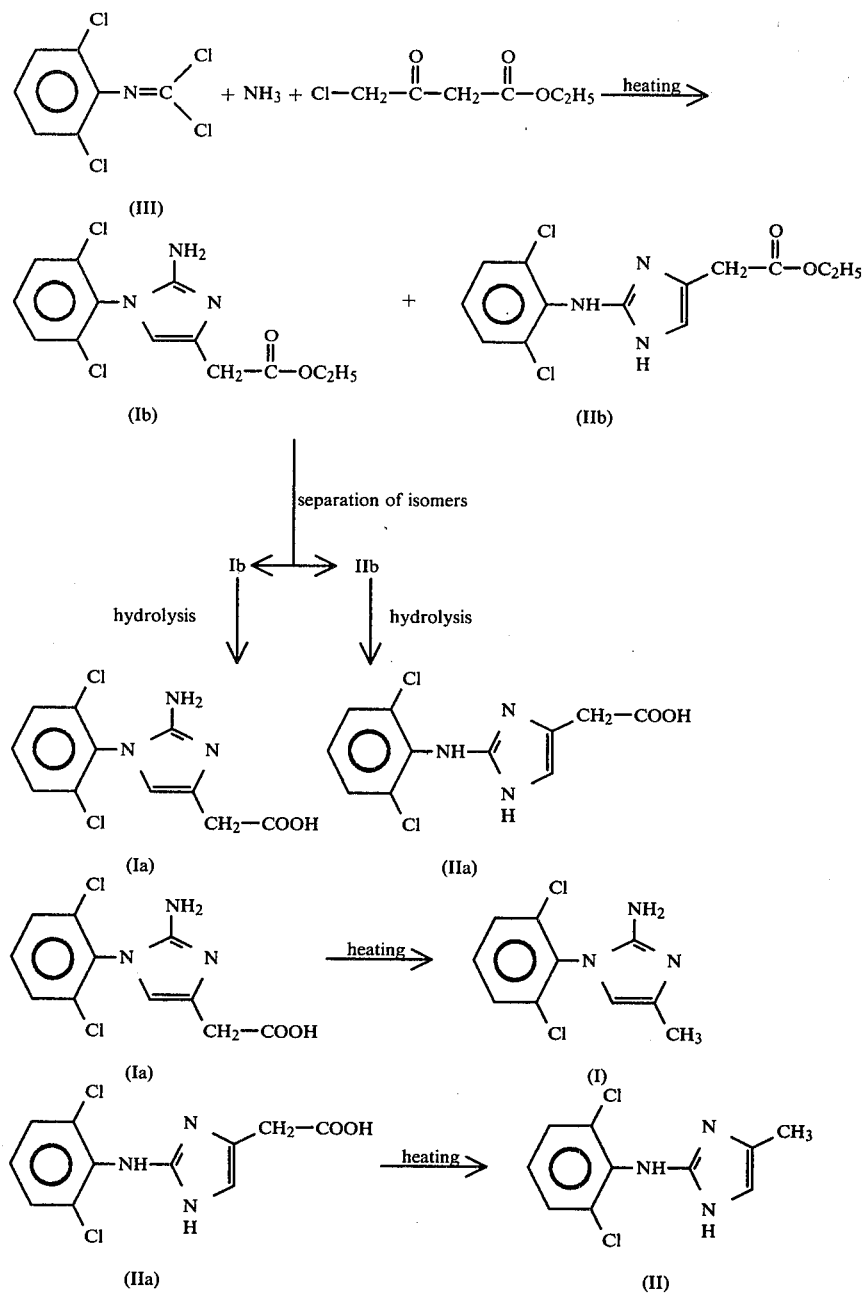

The non-toxic, pharmaceutically acceptable acid addition salts of isomeric compounds I and II may be obtained by conventional techniques. Thus, for example, an acid addition salt may be prepared by dissolving isomeric compound I and II in an organic solvent such as ethyl acetate. To the solution is added a mixture of an alkanol (e.g., isopropanol) and a hydrohalogen acid (e.g., hydrochloric acid) until acid reaction. The hydrochloride salt crystallizes from the solution and may be collected by filtration. The term "non-toxic, pharmaceutically acceptable" is used herein to indicate those salts containing anions which are relatively safe to the mammal and which do not exhibit side effects that detract from the beneficial properties of the salt.

The following examples illustrate the preparation of isomeric compounds I and II and the preparation of the novel ester and acid intermediates. It is to be understood, however, that the present invention is not limited to the details set forth in the examples.

Examples I-V illustrate the preparation of isomeric compounds I and II from various starting materials via the first process. Examples VI-XIII illustrate the preparation of isomeric compounds I and II, including the novel intermediates thereof, using the second process. The preparation of an acid addition salt of compound I is also illustrated in Example XII.

EXAMPLE I 10 grams of 2,6-dichlorophenyl isocyanide dichloride is dissolved in 50 ml of absolute ethanol. Into the mixture is passed gaseous ammonia at room temperature for one hour. 3.8 grams of chloroacetone in 30 ml of absolute ethanol is then added dropwise to the reaction mixture while continuing the introduction of ammonia. After the addition of the chloroacetone, the temperature of the reaction mixture is raised to its boiling point and, at this temperature, ammonia is passed into the solution for another 2 hours. The mixture is then evaporated to dryness under reduced pressure of from about 20 to about 50 m.m.Hg.

The residue is dissolved in a mixture of dilute hydrochloric acid and ethyl acetate (1:1). The ethyl acetate phase is separated and the aqueous phase is made alkaline with ammonia and is extracted with chloroform. The chloroform extract is evaporated to dryness.

In this manner, a mixture of crude 1-(2',6'-dichlorophenyl)-2-amino-4-methyl-imidazole (I) and 2-(2',6'-dichloroanilino)-4-methyl-imidazole (II) is obtained. The components are separated by chromatography using a column of silica gel and first ethyl acetate and then methanol as elutants.

EXAMPLE II

The procedure of Example I is repeated except that S-methyl-2,6-dichlorophenyl isothiuronium iodide is used in place of 2,6-dichlorophenyl isocyanide dichloride. After separation, isomeric compounds I and II are obtained.

EXAMPLE III

The procedure of Example I is repeated except that 2,6-dichlorophenyl cyanamide is used in place of 2,6-dichlorophenyl isocyanide dichloride. After separation, isomeric compounds I and II are obtained.

EXAMPLE IV

The procedure of Example I is repeated except that 2,6-dichlorophenyl guanidine is used in place of 2,6-dichlorophenyl isocyanide dichloride. After separation, isomeric compounds I and II are obtained.

EXAMPLE V

The procedure of Example I is repeated except that an equimolar mixture of 2,6-dichlorophenyl isocyanide dichloride and 2,6-dichlorophenyl guanidine is used in place of 2,6-dichlorophenyl isocyanide dichloride. After separation, isomeric compounds I and II are obtained.

EXAMPLE VI 7.2 grams of 2,6-dichlorophenyl isocyanide dichloride is dissolved in 30 ml of absolute ethanol by stirring. Into the stirred solution is passed gaseous ammonia for about one hour. 7.2 grams of 4-chloroacetoacetic acid ethyl ester is dissolved in 30 ml of absolute ethanol and the solution is added dropwise to the reaction mixture at room temperature while continuing the introduction of ammonia. The temperature of the reaction mixture is raised to the boiling point, and into the boiling reaction mixture is passed ammonia for another 6 hours. The mixture is cooled, filtered and the mother liquor is evaporated to dryness.

The solid residue is dissolved in a mixture of dilute hydrochloric acid and ethyl acetate. The ethyl acetate layer is separated and the aqueous layer is washed once with ethyl acetate. The aqueous layer is rendered alkaline with gaseous ammonia and the separated organic layer is extracted several times with chloroform. The combined chloroform extracts are washed with water, dried over $Na_2SO_4$ and evaporated to dryness under reduced pressure. The solid residue is triturated with warm ethyl acetate, cooled and filtered. The filter residue comprises a mixture of 4-[1-(2',6'-dichlorophenyl)-2-amino]-imidazoleacetic acid ethyl ester and 4-[2-(2',6'-dichloroanilino)]-imidazoleacetic acid ethyl ester.

The filter residue is dissolved in a mixture of acetone and ethyl acetate and into the solution is passed gaseous hydrogen chloride until the solution is acidified. The solution is cooled and filtered to yield a filter residue and liquor. The filtered precipitate is substantially pure 4-[2-(2',6'-dichloroanilino)]-imidazoleacetic acid ethyl ester hydrochloride having a melting point of about 221°–223° C.

The remaining liquor is evaporated to dryness and the residue is dissolved in water. The solution is rendered alkaline with gaseous ammonia and is filtered. The filtered precipitate is 4-[1-(2',6'-dichlorophenyl)-2-amino]-imidazoleacetic acid ethyl ester, which is purified by recrystallization from n-butyl acetate. The melting point of the product is about 125°–127° C.

4-[2-(2',6'-dichloroanilino)]-imidazoleacetic acid ethyl ester is obtained as a free base by dissolving the 4-[2-(2',6'-dichloroanilino)]-imidazoleacetic acid ethyl ester hydrochloride, prepared as described above, in water and making the aqueous solution alkaline with ammonia. 4-[2-(2',6'-dichloroanilino)]-imidazoleacetic acid ethyl ester precipitates as a free base, having a melting point of about 159°–161° C.

EXAMPLE VII

The procedure of Example V is repeated except that S-methyl-2,6-dichlorophenyl isothiuronium iodide is used in place of 2,6-dichlorophenyl isocyanide dichloride. The ester intermediates are obtained.

EXAMPLE VIII

The procedure of Example V is repeated except that 2,6-dichlorophenyl cyanamide is used in place of 2,6-dichlorophenyl isocyanide dichloride. The ester intermediates are obtained.

EXAMPLE IX

The procedures of Example V is followed except that 2,6-dichlorophenyl guanidine is used in place of 2,6-dichlorophenyl isocyanide dichloride. The ester intermediates are obtained.

EXAMPLE X 10 grams of 4-[1-(2',6'-dichlorophenyl)-2-amino]-imidazoleacetic acid ethyl ester is suspended in 50 ml of 6 N hydrochloric acid. The reaction mixture is boiled for one hour and is then cooled and filtered. The precipitate which consists of 4-[1-(2',6'-dichlorophenyl)-2-amino]-imidazoleacetic acid hydrochloride can be recrystallized from water. The melting point of the product is about 278°–283° C.

EXAMPLE XI 10 grams of 4-[2-(2',6'-dichloroanilino)]-imidazoleacetic acid ethyl ester is suspended in 50 ml of 6 N hydrochloric acid. The reaction mixture is boiled for one hour, cooled and neutralized with ammonia. The precipitate, which is 4-[2-(2',6'-dichloroanilino)]-imidazoleacetic acid, is filtered, washed with water and dried. The melting point of the product point is about 151°–152° C.

EXAMPLE XII 10 grams of 4-[1-(2',6'-dichlorophenyl)-2-amino]-imidazoleacetic acid is suspended in 50 ml of concentrated hydrochloric acid. The reaction mixture is refluxed with stirring for 4 hours and is cooled and rendered alkaline with sodium hydroxide solution. The product is extracted with chloroform and the chloroform extract is evaporated to dryness. The obtained 1-(2',6'-dichlorophenyl)-2-amino-4-methyl-imidazole is recrystallized from isopropanol to yield a product having a melting point of about 195°–198° C.

For preparing the hydrochloride acid addition salt the product is dissolved in ethyl acetate. A HCl-isopropanol solution is added until acid reaction occurs. The hydrochloride acid addition salt crystallizes out and is collected by filtration.

EXAMPLE XIII 10 grams of 4-[2-(2',6'-dichloroanilino)]-imidazoleacetic acid is suspended in 50 ml of concentrated hydrochloric acid. The reaction mixture is refluxed with stirring for 8 hours and is cooled and rendered alkaline with sodium hydroxide. The product is extracted with chloroform and the chloroform extract is evaporated to dryness. The obtained 2-(2',6'-dichloroanilino)-4-methyl-imidazole has a melting point of about 110°–115° C.

As stated above, isomeric compounds I and II and their non-toxic, pharmaceutically acceptable acid addition salts have valuable pharmacological properties and have been shown to possess excellent anti-hypertensive activity in mammals. This activity makes the imidazole derivatives particularly useful in the treatment of high blood pressure. Preliminary tests have shown that they also possess anti-convulsant, anti-depressant, analgesic, anti-inflammatory, anti-ulcer and anti-arrhythmic activity.

Administration of isomeric compounds I or II, their non-toxic, pharmaceutically acceptable acid addition salts or mixtures thereof may be achieved either parenterally or orally. Typically, an effective amount of the derivative is combined with a suitable pharmaceutical carrier. As used herein, the term "effective amount" encompasses those amounts which yield the desired activity without causing adverse side-effects. Although the precise amount employed in a particular situation is dependent upon numerous factors such as method of administration, type of mammal, etc., the daily dose generally ranges from about 5 to about 50 milligrams per kilogram of mammal.

The pharmaceutical carriers which are typically employed with the derivatives may be solid or liquid and are generally selected dependent on the planned manner of administration. Thus, for example, solid carriers include lactose, sucrose, gelatin and agar, while liquid carriers include water, syrup, peanut oil and olive oil. The combination of the derivative and the carrier may be fashioned into numerous acceptable forms such as tablets, capsules, suppositories, solutions, emulsions and powders.

The anti-hypertensive properties of the imidazole derivatives of the invention may be shown by using anesthetized Sprague-Dawley rats of normal weight. The test animals are first anesthetized with urethane. After this the femoral artery is connected by way of a polyethylene tube with a blood pressure transducer. The test substance is injected into the femoral vein. The blood pressure and the pulse frequency are registered with a recorder.

In a further test unanesthetized Okamoto-Aoki spontaneous hypertensive rats (SHR) are used. The test derivative is administered perorally by way of a tube into the stomach. The blood pressure is measured from the tail using an indirect bloodless method.

The result of these tests is shown in Table 1.

TABLE 1

| Compound | Dosage | Kind of rats used | No. of rats | Average reduction of blood pressure | Average reduction of pulse frequency |
|---|---|---|---|---|---|
| 1-(2',6'-dichloro-phenyl)-2-amino-4-methyl-imidazole | 3,3 mg/kg i.v. | anesthetized Sprague-Dawley rats | 10 | 20 percent | |
| (compound I) | 10 mg/kg i.v. | anesthetized Sprague-Dawley rats | 10 | 25 percent | 20 percent |
| | 100 mg/kg p.o. | SHR rats | 9 | 35 percent | |
| 2-(2',6'-dichloro-anilino)-4-methyl-imidazole (compound II) | 10 mg/kg i.v. | anesthized Sprague-Dawley rats | 9 | 25 percent | |

The reduction of the blood pressure with compounds I and II is smooth and of relatively long duration. No temporary rise of the blood pressure is observed at the beginning of the administration contrary to this undesirable side effect found in some imidazole derivatives, e.g., clonidine. The compounds are also noted by their low toxicity. Thus, the $LD_{50}$ in rats of the compound I is 30 mg/kg i.v. and 250 mg/kg p.o.

To demonstrate the anti-ulcer activity of compound I, tests are conducted on female rats which had been fasting overnight. Gastric ulcers are induced by anti-inflammatory agents (e.g., indomethacin) and simultaneously compound I is administered i.p. After three hours the rats are killed and the number of gastric ulcers counted. The results indicate that compound I prevents the formation of gastric ulcers in doses on the order of 20 mg/kg i.p., and is effective in reducing the number of ulcers in doses as small as 1 mg/kg i.p.

The novel intermediates described above, namely 4-[1-(2',6'-dichlorophenyl)-2-amino]-imidazoleacetic acid, 4-[2-(2',6'-dichloroanilino)]-imidazoleacetic acid, 4-[1-(2',6'-dichlorophenyl)-2-amino]-imidazoleacetic acid lower alkyl ester, and 4-[2-(2',6'-dichloroanilino)]-imidazoleacetic acid lower alkyl ester have further been found to exhibit significant diuretic activity. In this capacity, the intermediates may be employed individually, as their respective non-toxic, pharmaceutically acceptable acid addition salts or as mixtures thereof.

Similar to what has been previously stated concerning the administration of compounds I and II, administration of the intermediates or their acid addition salts or mixtures thereof may be achieved either parenterally or orally. Typically, an effective amount of the derivative is combined with one or more of the exemplary pharmaceutical carriers mentioned above. As used with regard to the intermediates, the term "effective amount" encompasses those amounts which yield activity without causing substantial adverse side-effects. Although the precise amount employed in a particular situation is dependent on numerous factors such as those mentioned above, the daily dose generally ranges from about 1 to about 50, perferably from about 2 to about 10, milligrams per kilogram of mammal. The non-toxic, pharmaceutically acceptable acid addition salts of the intermediates may also be utilized at the same dosage level, which salts can be obtained by conventional techniques mentioned above in regard to the isomer compounds.

The diuretic activity of the intermediates may be shown by the following Example.

EXAMPLE XIV

The diuretic effect of the intermediates may be studied by injecting the compounds intraperitoneally to adult Sprague-Dawley male rats after an overnight fast. Simultaneously, 10 ml of water is fed to each rat through a gastric tube. The mean values of urine volume obtained are shown in Table 2.

TABLE 2

| Compound | Dosage mg/kg | Number of Rats | Hours | Mean Cumulative Volume of Urine (ml) | | | | |
|---|---|---|---|---|---|---|---|---|
| | | | | 0-1 | 0-2 | 0-3 | 0-4 | 0-5 |
| Ia | 2 | 6 | | 2.6 | 10.2 | 13.9 | 14.7 | 16.4 |
| Ib | 2 | 6 | | 2.3 | 10.9 | 12.3 | 14.5 | 15.7 |
| IIa | 2 | 6 | | 1.3 | 8.1 | 12.9 | 14.3 | 14.9 |
| IIb | 2 | 6 | | 3.4 | 9.5 | 13.4 | 14.4 | 14.4 |
| Saline (control) | | 6 | | 1.1 | 7.2 | 11.4 | 13.5 | 13.5 |

In Table 2:
Compound Ia is 4-[1-(2',6'-dichlorophenyl)-2-amino]-imidazoleacetic acid
Compound Ib is 4-[1-(2',6'-dichlorophenyl)-2-amino]-imidazoleacetic acid ethyl ester
Compound IIa is 4-[2-(2',6'-dichloroanilino)]-imidazoleacetic acid
Compound IIb is 4-[2-(2',6'-dichloroanilino)]-imidazoleacetic acid ethyl ester As may be seen from the Table, the diuretic effects of these compounds is quite pronounced particularly in the first two hours after treatment which is the time in which this effect is desired. Of these intermediates, the 4-[2-(2',6'-dichloroanilino)]-imidazoleacetic acid ethyl ester is preferred.

The acid addition salts, e.g., 4-[2',6'-dichloroanilino)]-imidazoleacetic acid ethyl ester hydrochloride, the preparation of which has been described above, may also be utilized with similar results, as may mixtures of the intermediates.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims.

What is claimed is:

1. A 2,6-dichlorophenyl-substituted amino-imidazole derivative having anti-hypertensive properties selected from the group consisting of 1-(2',6'-dichlorophenyl)-2-amino-4-methyl-imidazole, its non-toxic, pharmaceutically acceptable acid addition salts and mixtures thereof.

2. The compound 4-[1-(2',6'-dichlorophenyl)-2-amino]-imidazoleacetic acid.

3. The compound 4-[2-(2',6'-dichloroanilino)]-imidazoleacetic acid.

4. The compound 4-[1-(2',6'-dichlorophenyl)-2-amino]-imidazoleacetic acid lower alkyl ester.

5. The compound 4-[2-(2',6'-dichloroanilino)]-imidazoleacetic acid lower alkyl ester.

6. A process for treating a mammal having a hypertensive condition comprising administering to said mammal an effective amount of a composition selected from the group consisting of 1-(2',6'-dichlorophenyl)-2-amino-4-methyl imidazole, its non-toxic, pharmaceutically acceptable acid addition salts and mixtures thereof.

7. The process of claim 6 wherein the composition is combined with a pharmaceutical carrier.

8. The process of claim 7 wherein the effective daily amount is from about 5 to about 50 milligrams for each kilogram of mammal.

9. A process for treating a mammal with an effective amount of a diuretic agent selected from the group consisting of 4-[1-(2',6'-dichlorophenyl)-2-amino]-imidazoleacetic acid, 4-[2-(2',6'-dichloroanilino)]-imidazoleacetic acid, 4-[1-(2',6'-dichlorophenyl)-2-amino]-imidazoleacetic acid lower alkyl ester, 4-[2-(2',6'-dichloroanilino)]-imidazoleacetic acid lower alkyl ester, their non-toxic pharmaceutically acceptable acid addition salts and mixtures thereof.

10. The process of claim 9 wherein the diuretic agent is selected from the group consisting of 4-[2-(2',6'-dichloroanilino)]-imidazoleacetic acid ethyl ester, its non-toxic, pharmaceutically acceptable acid addition salts and mixtures thereof.

11. The process of claim 9 wherein the composition is combined with a pharmaceutical carrier.

12. The process of claim 9 wherein the effective daily amount is from about 1 to about 50 milligrams for each kilogram of mammal.

* * * * *